United States Patent [19]

Cohen et al.

[11] Patent Number: 5,079,228
[45] Date of Patent: Jan. 7, 1992

[54] PEPTIDE INHIBITORS OF NEUTROPHIL ACTIVATING FACTOR INDUCED CHEMOTAXIS

[75] Inventors: Allen B. Cohen, Tyler; Edmund J. Miller, Flint; Shigeki Nagao; Ferdicia K. Carr, both of Tyler, all of Tex.

[73] Assignee: Board of Regents, The University of Texas System, Austin, Tex.

[21] Appl. No.: 475,658

[22] Filed: Feb. 5, 1990

[51] Int. Cl.$^5$ .................. C07K 7/08; C07K 7/10; A61K 37/02
[52] U.S. Cl. ........................ 514/12; 514/13; 530/324; 530/326
[58] Field of Search ............. 530/324, 326; 514/12, 514/13

[56] References Cited

FOREIGN PATENT DOCUMENTS

89/04836 6/1989 PCT Int'l Appl. .

OTHER PUBLICATIONS

Article in Wall Street Journal by David Stipp, Heart Attack Studies Spark a Scramble Among Drug Firms for New Medicines, Section B4, Nov. 20, 1989.
Gianetto and DeDuve, Comparative Study of the Binding of Acid Phosphatase β-Glucuronidase and Cathepsin by Rat–Liver Particles, Bioch. 59, pp. 443–438, 1955.
Sticherling et al., Production and Characterization of Monoclonal Antibodies Against the Novel Neutrophil Activating Peptide NAP/IL-8, J. of Immumology, vol. 143, pp. 1628–1634, No. 5, Sep. 1, 1989.
A. Boyum, Isolation of Mononuclear Cells and Granulocytes from Human Blood, Scand. J. Clin. Lab. Invest. 21, Supp. 97, p. 77 (1968).
Cohen et al., The Release of Elastase, Myeloperoxidase, and Lysozyme from Human Alveolar Macrophages, Am. Rev. Respir. Dis., vol. 126, pp. 241–247 (1982).
MacArthur et al., A Peptide Secreted by Human Alveolar Macrophages Releases Neutrophil Granule Contents, J. of Immunology, vol. 139, pp. 3456–3462, No. 10, Nov. 15, 1987.
Cohen et al., A Peptide from Alveolar Macrophages that Releases Neutrophil Enzymes into the Lungs in Patients with the Adult Respiratory Distress Syndrome, Am. Rev. Respir. Dis., vol. 137, pp. 1151–1158 (1988).
Zigmond and Hirsch, New Methods for Evaluation and Demonstration of a Cell-Derived Chemotactic Factor, J. of Exp. Med., vol. 137, p. 387–410 (1973).
Goldstein et al., Mechanisms of Lysosomal Enzyme Release from Human Leukocytes: Microtubule Assembly and Membrane Fusion Induced by a Component of Complement, Proc. Natl. Acad. Sci. USA, vol. 70, #10, pp. 2916–2920, Oct. 1973.
Snyderman et al., Chemotaxis of Mononuclear Cells, Academic Press, New York, pp. 651–661 (1976).
Tanaka et al., Synthesis and Biological Characterization of Monocyte-Derived Neutrophil Chemotactic Factor, FEBS Letters, vol. 236, No. 2, pp. 467–470, Aug. 1988.
Suzuki et al., Localization of Chemotactic Activity and 64 kD Protein Phosphorylation for Human Polymorphonuclear Leukocytes in N-Terminus of the Chemotactic Protein LUCT/IL-8, Biochem. and Biophy. Research Comm., vol. 163, No. 3 (1989).

(List continued on next page.)

Primary Examiner—Lester L. Lee
Assistant Examiner—Avis M. Davenport
Attorney, Agent, or Firm—Arnold, White & Durkee

[57] ABSTRACT

The present invention describes a method of preventing neutrophil chemotaxis, either in vitro or at a biological site using peptides whose amino acid sequence is derived at least in part from the sequence of native neutrophil activating factor (NAF). The peptides do not have measurable chemotactic activity against human neutrophils, but they are antagonistic to native NAF. The method of preventing neutrophil chemotaxis is practiced by adding sufficient amounts of the claimed peptides to neutrophils in a biological fluid or appropriate medium to inhibit neutrophil chemotaxis. The claimed peptides may have therapeutic value in patients with Adult Respiratory Distress Syndrome (ARDS) or with other inflammatory lesions known or found to be caused by NAF.

20 Claims, 4 Drawing Sheets

OTHER PUBLICATIONS

McGuire et al., Studies on the Pathogenesis of the Adult Respiratory Distress Syndrome, J. Clin. Invest., vol. 69, pp. 543-553, Mar. 1983.

Idell et al., Bronchoalveolar Lavage in Patients with the Adult Respiratory Distress Syndrome, Clinics in Chest Medicine, vol. 6, No. 3, pp. 459-471, Sep. 1985.

Idell et al., Neutrophils Elastase-Releasing Factors in Bronchoalveolar Lavage from Patients with Adult Respiratory Distress Syndrome, Am. Rev. Respir. Dis., vol. 132, pp. 1098-1105 (1985).

Carpenter et al., Phorbol Myristate Acetate Produces Injury to Isolated Rat Lungs in the Presence and Absence of Perfused Neutrophils, Toxicology and Applied Pharmacology, vol. 91, pp. 22-32 (1987).

Fox et al., Pulmonary Inflammation Due to Oxygen Toxicity: Involvement of Chemotactic Factors and Polymorphonuclear Leukocytes, Am. Rev. Respir. Dis., vol. 123, pp. 521-523 (1981).

Article by Thelen et al., Mechanism of Neutrophil Activation by NAF, a Novel Monocyte-Derived Peptide Agonist, FJ Research Communications, pp. 2702-2706, 1988.

Article by Yoshimura et al., Purification of a Human Monocyte-Derived Neutrophil Chemotactic Factor that has Peptide Sequence Similarity to the Other Host Defense Cytokines, Proc. Natl. Acad. Sci. USA, vol. 84, pp. 9233-9237, Dec. 1987.

Article by Walz et al., Purification and Amino Sequencing of NAF, a Novel Neutrophil-Activating Factor Produced by Monocytes, Biochemical and Biophysical Research Communications, vol. 143, No. 2, pp. 755-761, 12/16/87.

Peveri et al., A Novel Neutrophil-Activating Factor Produced by Human Mononuclear Phagocytes, J. Exp. Med., vol. 167, pp. 1547-1559, May 1988.

Willems et al., Human Granulocyte Chemotactic Peptide (IL-8) as a Specific Neutrophil Degranulator: Comparison with Other Monokines, Immunology, vol. 67, pp. 540-542 (1989).

Lindley et al., Synthesis and Expresson in *Escherichia coli* of the Gene Encoding Monocyte-Derived Neutrophil-Activating Factor: Biological Equivalence Between Natural and Recombinant Neutrophil-Activating Factor, Proc. Natl. Acad. Sci. USA, vol. 85, pp. 9199-9203, Dec. 1988.

Van Damme et al., A Novel, $NH_2$-Terminal Sequence-Characterized Human Monokine Possessing Neutrophil Chemotactic, Skin-Reactive, and Granulocytosis-Promoting Activity, J. Exp. Med., vol. 167, pp. 1364-1376, Apr. 1988.

Oppenheim et al., Relationship Between Interleukin 1 (IL1), Tumor Necrosis Factor (TNF) and a Neutrophil Attacting Peptide (NAP-1), Agents amd Actions, vol 26, ¼ (1989), pp. 134-140.

Schroder et al., Purification and Partial Biochemical Characterization of a Human Monocyte-Derived, Neutrophil-Activating Peptide that Lacks Interleukin 1 Activity, J. of Immunology, vol. 139, #10, Nov. 15, 1987, p. 3474.

Larsen et al., The Neutrophil-Activating Protein (NAP-1) is Also Chemotactic for T Lympocytes, Science, vol. 243, pp. 2464-1466, Jan. 1989.

Schmid and Weissmann, Induction of mRNA for a Serine Protease and $\beta$-Thromboglobulin-Like Protein in Mitogen-Stimulated Human Leukocytes, J. of Immunology, vol. 139, pp. 250-256 (1987).

Mukaida et al., Genomic Structure of the Human Monocyte-Derived Neutrophil Chemotactic Fctor IL-8, J. of Immunology, vol. 143, pp. 1366-1371, No 4, Aug. 15, 1989.

Kowalski and Denhardt, Regulation of the mRNA for MONAP, an Inflammatory Response Monokine, in Differentiating HL60 Promyelocytes, Molecular and Cellular Biology, vol. 9, No. 5, pp. 1946-1957, May 1989.

Matsushima et al., Molecular Cloning of a Human Monocyte-Derived Neutrophil Chemotactic Factor (MDNCF) and the Induction of MDNCF mRNA by Interleukin 1 and Tumor Necrosis Factor, J. Exp. Med., vol. 167, Jun. 1988.

PEPTIDE INHIBITORS OF NEUTROPHIL ACTIVATING FACTOR INDUCED CHEMOTAXIS

BACKGROUND OF THE INVENTION

1. Field of the Invention

This invention pertains to peptide inhibitors of Neutrophil activating factor induced human neutrophil chemotaxis, and more particularly to inhibitors having their sequence in part identical to that of neutrophil activating factor. These inhibitors have potential use in preventing chemotactic behavior of neutrophils in biological fluids and thereby reducing the injury that the neutrophils cause in diverse disease states such as the adult respiratory distress syndrome.

Table 1 is a list of abbreviations used for the amino acids comprising the peptides

TABLE 1

| A | ala | alanine |
|---|-----|---------|
| B | asx | (asparagine or aspartic acid) |
| C | cys | cysteine |
| D | asp | aspartic acid |
| E | glu | glutamic acid |
| F | phe | phenylalanine |
| G | gly | glycine |
| H | his | histidine |
| I | ile | isoleucine |
| K | lys | lysine |
| L | leu | leucine |
| M | met | methionine |
| N | asn | asparagine |
| P | pro | proline |
| Q | gln | glutamine |
| R | arg | arginine |
| S | ser | serine |
| T | thr | threonine |
| V | val | valine |
| W | trp | tryptophan |
| Y | tyr | tyrosine |
| Z | glx | (glutamic acid or glutamine) |

2. Description of Related Art

Neutrophil activating factor (NAF) is a peptide produced by stimulated human monocytes. It is chemotactic for human neutrophils, but not lymphocytes, platelets, or monocytes.[1-4] NAF is medically of particular interest as a potential intervention point for prevention or treatment of Adult Respiratory Distress Syndrome (ARDS).

Native NAF appears to be released in vivo in response to some forms of stress, and may be the cause of the observed neutrophil influx noted in lung fluid occurring early in the course of ARDS. Neutrophils are thought to cause lung damage which may result in death. An agent which would inhibit the chemotactic effects of NAF, without itself inducing chemotaxis, has potential application not only in ARDS but also other forms of inflammation that may be caused by NAF and in the in vitro and in vivo study of the effects of NAF.

Neutrophils have been implicated in tissue damage occurring after heart attacks. Normally employed to fight invading microorganisms, neutrophils may actually damage healthy tissue or recovering tissue because of release of substances intended to attack foreign matter. When accumulating at the site of an inflammation, neutrophils may actually block tiny blood vessels and in the heart cause severe post-heart attack tissue damage.[5] Several research groups are actively exploring the development of drugs to prevent neutrophils from adhering to vessel walls. Approaches include the use of antibodies to "coat" the neutrophils and drugs that prevent activation of neutrophils.

NAF is known by several different names, including NAP-1,[6] MONAP,[7] MCDNF,[2] LYNAP 9110 and GCP.[4] The name interleukin-8 (IL-8) has been proposed for this molecule.[8]

NAF has been described and partially sequenced virtually simultaneously by three laboratories.[2-4] Two groups[2, 4] noted that the sequence was identical to that inferred from the cDNA of protein 3-10C induced in peripheral leukocytes by Staphylococcal enterotoxin A.[9] The full genomic sequence encoding for NAF is now known[10] and the regulation of the mRNA for NAF has been investigated.[11,12] Tumor necrosis factor and interleukin-1 induced NAF gene transcription in monocytes after one hour of exposure, and secretion was induced between 1 and 6 hours of exposure. Interferons gamma and alpha had no effect on the gene transcription.[12]

The function of NAF is dependent on GTP-binding proteins.[1] This leads to activation of protein kinase and to a transient increase in cytostolic $Ca^{++}$. Surface receptors apparently are different from those of other chemotactic agents such as leukotriene $B_4$, platelet activating factor, C5a and FMLP.[13]

There have been conflicting reports on the ability of NAF to initiate neutrophil degranulation. Schröder et al.[7] reported the release of beta-glucuronidase from neutrophil primary granules while Willems et al.[14] showed that NAF did not induce significant release of this enzyme activity.

NAF has been isolated, sequenced and purified. Its main form has been produced from a gene synthesized, cloned and expressed in *E. Coli*.[15] Four antibodies against NAF have been produced and characterized and then used to show cross reactivity with partially homologous peptides.[16] All antibodies could be used in an immunoaffinity column to isolate a 10 kDa protein having NAP/IL-8 activity. This peptide, as well as two others having the same chemotactic activity, have been sequenced. The other peptides, described as variants of the main form, differ in having seven and five additional amino acids respectively at the N-terminus relative to the main form.[2]

SUMMARY OF THE INVENTION

The present invention involves a method of preventing neutrophil chemotaxis, either in vitro or at a biological site, using peptides whose amino acid sequence is derived at least in part from the sequence of native neutrophil activating factor. The peptides do not have measurable chemotactic activity against human neutrophils, but they are antagonistic to naturally occuring neutrophil activating factor. The method of preventing neutrophil chemotaxis is practiced by adding enough of one or more of the claimed peptides to neutrophils in a biological fluid or appropriate media to inhibit neutrophil chemotaxis.

In a particular embodiment of the invention, a synthetic peptide having the amino acid sequence KELRCQCIKTYSKPFHPKFIKEL is added to a neutrophil-containing solution. In a most preferred embodiment, the cited peptide and a peptide having the sequence SDGRELCLDPKENWVQRVVEKFLKRAENS are added to the neutrophil solution.

Other peptides derived at least in part from the amino acid sequence of native neutrophil activating factor and antagonistic to neutrophil activating factor could be used if shown to prevent neutrophil chemotaxis.

The invention claims the novel peptides having the sequence KELRCQCIKTYSKPFHPKFIKEL and SDGRELCLDPKENWVQRVVEKFLKRAENS. The peptides are antagonistic toward NAF and do not have measurable NAF chemotactic activity.

DESCRIPTION OF THE PREFERRED EMBODIMENTS

Studies were conducted in which several overlapping sequences of the amino acids in NAF were synthesized. Two peptides made of sequences contained within NAF were found to interfere with the chemotactic activity of the native molecule. Neither of these peptides was chemotactic. Peptides NAF (3-25) and NAF (44-72) were both found to reduce the action of native NAF and were found to be approximately additive in their effects. The respective structures of these peptides are KELRCQCIKTYSKPFHPKFIKEL and SDGRELCLDPKENWVQRVVEKFLKRAENS.

This is the first demonstration that a peptide containing a portion of the amino acid sequence of NAF is both an antagonist of NAF without detectable neutrophil chemotactic activity.

EXAMPLES

Peptide Synthesis

Five overlapping peptides were synthesized and designated according to their correspondence to the native molecule. The peptide sequences were as follows: NAF (3-25), KELRCQCIKTYSKPFHPKFIKEL; NAF (19-32), PKFIKELRVIESGP; NAF (25-43), LRVIESGPHCANTEIIVKL; and NAF (35-55), ANTEIIVKLSDGRELCLDPKE; NAF (44-72), SDGRELCLDPKENWVQRVVEKFLKRAENS.

NAF (19-32) was synthesized at The University of Texas Health Center at the Tyler (UTHCT) core facility by Dr. D. K. Blumenthal. The other peptides were synthesized by Advanced Chem Tech, Inc. (Louisville, Ky.).

Each of the peptides was synthesized using t-BOC solid phase methodology. Each peptide eluted in a single peak from a reverse phase high performance liquid chromatography column under the influence of a linear gradient. (Solvent A: 0.1% Trifluoroacetic acid (TFA), Solvent B: 90% Acetonitrile/Water +0.09% TFA, Gradient 0% B to 60% B in 30 min). The amino acid sequences were confirmed on an Applied Biosystems Model 477A liquid pulse sequencer with an on-line 120A amino acid analyzer (Foster City, Calif.) by the protein biochemistry core facility of the UTHCT.

A total of five overlapping peptides NAF; (3-25), NAF (19-32), NAF (25-43), NAF (35-55) and NAF (44-72) were synthesized.

Figure 1:
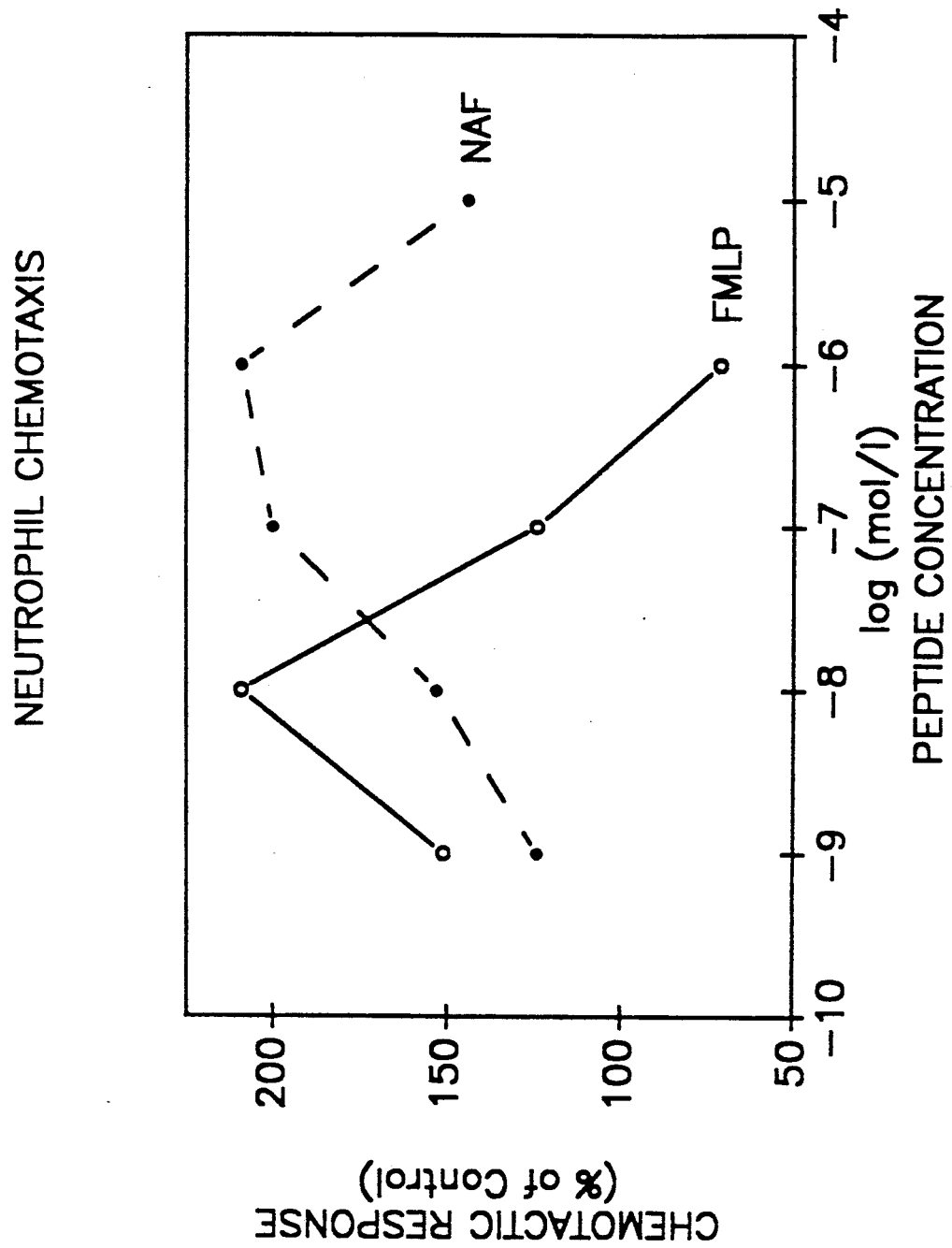
FIG. 1 is a comparison of neutrophil chemotactic activities of NAF and FMLP. The graph shows a representative experiment from six assays.
Figure 2:
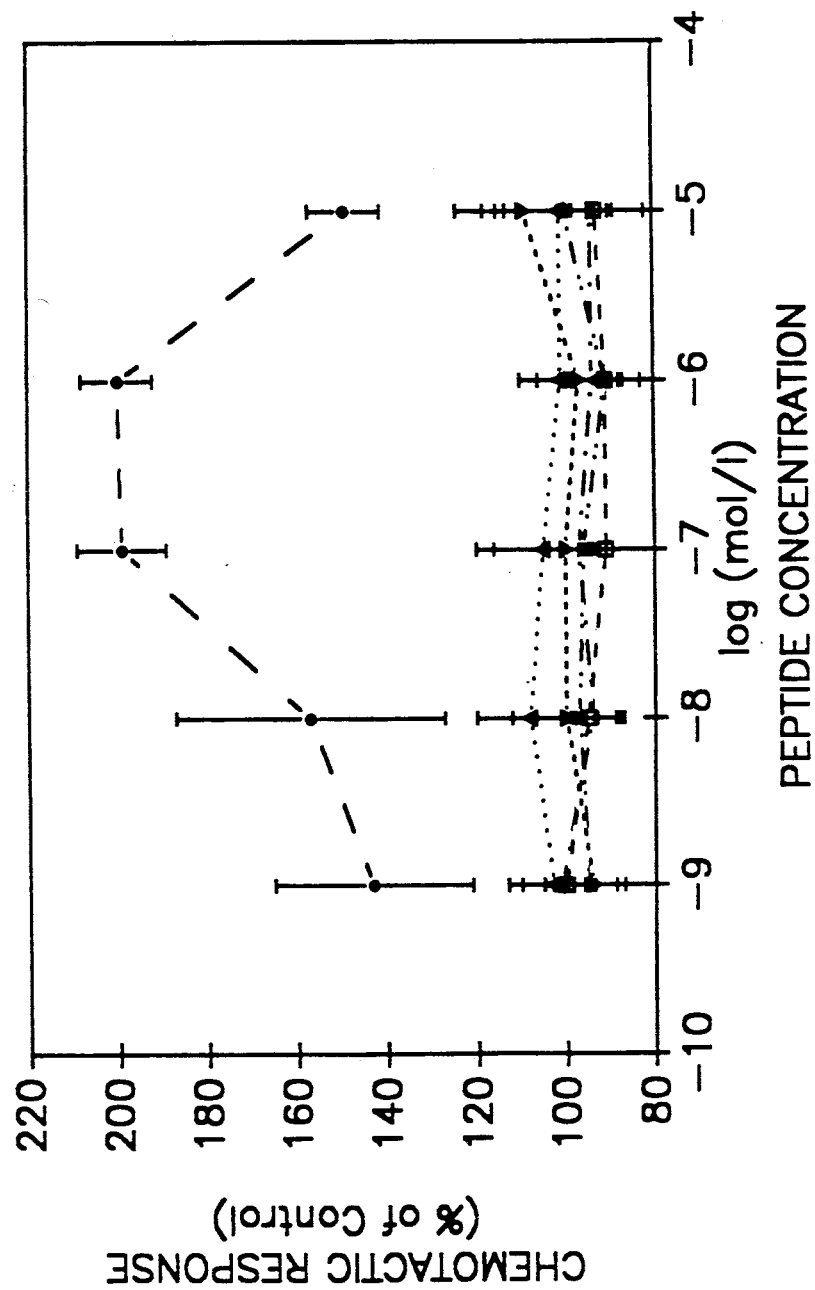
FIG. 2 shows a comparison of neutrophil chemotactic activities of NAF (- - -) and five synthetic NAF peptides (. . . , individually represented). The graph represents the data from six experiments.

Each of the peptides was assayed for its ability to induce the directed migration of neutrophils towards itself. Neutrophils exhibit random, chemokinetic movement when incubated in RPMI-1640 medium plus albumin alone. The distances migrated by the cells, under the influence of the various peptides, was therefore expressed as a percentage of the distance travelled in RPMI tissue culture medium alone. In the first experiments the effect of native NAF on the cells was compared to that of FMLP (FIG. I). Both of these peptides increase the cell migration at a peptide concentration of $1 \times 10^{-9}$M and both peptides exhibit a prophase at higher concentrations (FIG. 1). None of the synthetic peptides induced chemotaxis either alone or in combination with one another when the synthetic peptides were examined under the same conditions (FIG. 2).

The peptides were examined to determine if any of the peptides could block the action of the native molecule. In these experiments the attractant in the lower well of the Boyden chamber contained both native NAF ($1 \times 10^{-8}$M) and one or more synthetic peptide(s) ($1 \times 10^{-6}$M) Table 2. The migration of the cells in RPMI tissue culture medium alone, or under the influence of native NAF or the individual peptides was also examined in each experiment. Two of the peptides NAF (3-25) and NAF (44-72) were both found to reduce the action of native NAF. The mean migration of native NAF was an average of 79% (S.D.=3) above that of buffer alone, while the mean migration towards native NAF in the presence of NAF (3-25) was 32% (S.D.=10) and the mean migration towards native NAF in the presence of NAF (44-72) (S.D.=13) was 52% above control migration (Table 2). These reductions are statistically significant at $p < 0.002$ by Student's t test. These two peptides inhibited NAF induced migration by 59 and 34% respectively. When NAF was incubated in the presence of both peptides the mean migration towards native NAF was 24% (S.D.=3) above controls for a total inhibition of NAF activity of 70%. Therefore, the inhibitory effects of the peptides were approximately additive. If the neutrophils were pre-incubated for ten minutes at room temperature before being added to the upper chamber the cells were found to be chemotactically unresponsive to the native NAF molecule. Furthermore, the inhibition was specific and the peptides did not interfere with the chemotaxis induced by FMLP, complement component C5a, or leukotriene B4.

Preparation of Neutrophils

Human blood was anticoagulated with heparin. Neutrophils were separated by dextran sedimentation and erythrocyte lysis by the method of Boyum[17] as modified in earlier studies.[18-20] Previous studies[18] showed that cell preparations containing 80-90% purity gave the same results as cells isolated to 90% purity by the Boyum method.

TABLE 2
INHIBITION OF NAF-INDUCED NEUTROPHIL CHEMOTAXIS[a]

| CHEMOTAXIS | DISTANCE MOVED (% of control) | INHIBITION (%) |
|---|---|---|
| RPMI-1640 | 100 | |
| NAF | 179 ± 3 | |
| NAF(3-25) | 100 ± 6 | |
| NAF(19-32) | 100 ± 11 | |
| NAF(25-43) | 94 ± 11 | |
| NAF(35-55) | 100 ± 2 | |
| NAF(44-72) | 97 ± 6 | |
| NAF + NAF(3-25) | 132 ± 10 | 59 ± 13[b] |
| NAF + NAF(19-32) | 187 ± 8 | — |
| NAF + NAF(25-43) | 181 ± 13 | — |
| NAF + NAF(35-55) | 190 ± 6 | — |
| NAF + NAF(44-72) | 152 ± 13 | 34 ± 16[b] |
| NAF + NAF(3-25) + NAF(44-72) | 124 ± 3 | 70 ± 4[b] |
| NAF + NAF(3-25)[c] | 97 ± 11 | 104 ± 14[b] |
| FMLP | 180 ± 17 | |
| FMLP + NAF(3-25) | 190 ± 18 | — |

[a]Concentrations of NAF = $1 \times 10^{-8}$M, FMLP = $5 \times 10^{-9}$M, and Peptide = $1 \times 10^{-6}$M
[b]Significantly different from NAF alone (P < 0.002) by t-test of means
[c]Neutrophils were preincubated with NAF(3-25).

Chemotaxis

Chemotaxis was performed using the leading front method as described by Zigmond and Hirsch.[21] The test material was placed in the lower well of a blind well chemotaxis chamber.[22] A five micron pore size, and 100 μl aliquot of the neutrophil preparation ($1 \times 10^6$ cells/ml) in RPMI-1640 containing 1% albumin was added to the top of the filter and incubated at 37° C. for 30 min. (In some experiments neutrophils were pre-incubated in the presence of peptide for 10 min at room temperature before being added to the upper chamber.) The filter was then fixed and stained and mounted on a glass microscope slide. The leading front was determined by the position of the leading two cells. The distance that the leading two cells had moved through the filter was measured for six fields on each filter. The measurements were made with two filters for each set of conditions.

Enzyme Release from Neutrophils

Neutrophil enzyme release was measured by a modification of the method of Goldstein and colleagues.[23] Cytochalasin B (Sigma Chemical Co., St. Louis, Mo.) was stored in dimethylsulphoxide at a concentration of 5 mg/ml and diluted to a concentration of 100 μg/ml in Hanks' balanced salt solution (HBSS) immediately before use. Neutrophils were prepared as described and incubated at a cell density of $5 \times 10^6$ cells/ml for ten minutes at room temperature in the presence of Cytochalasin B (10 μg/ml). Aliquots of 100 μl of the primed cell suspension were then distributed into the wells of a 96-well microtiter plate and 100 μl of stimulant was added. The cells were then incubated at 37° C. for 30 min. The plates were centrifuged at 850 rpm for 5 min, and 100 μl of supernatant was removed. The supernatants were assayed for β-D-glucuronidase activity.

Figure 3:
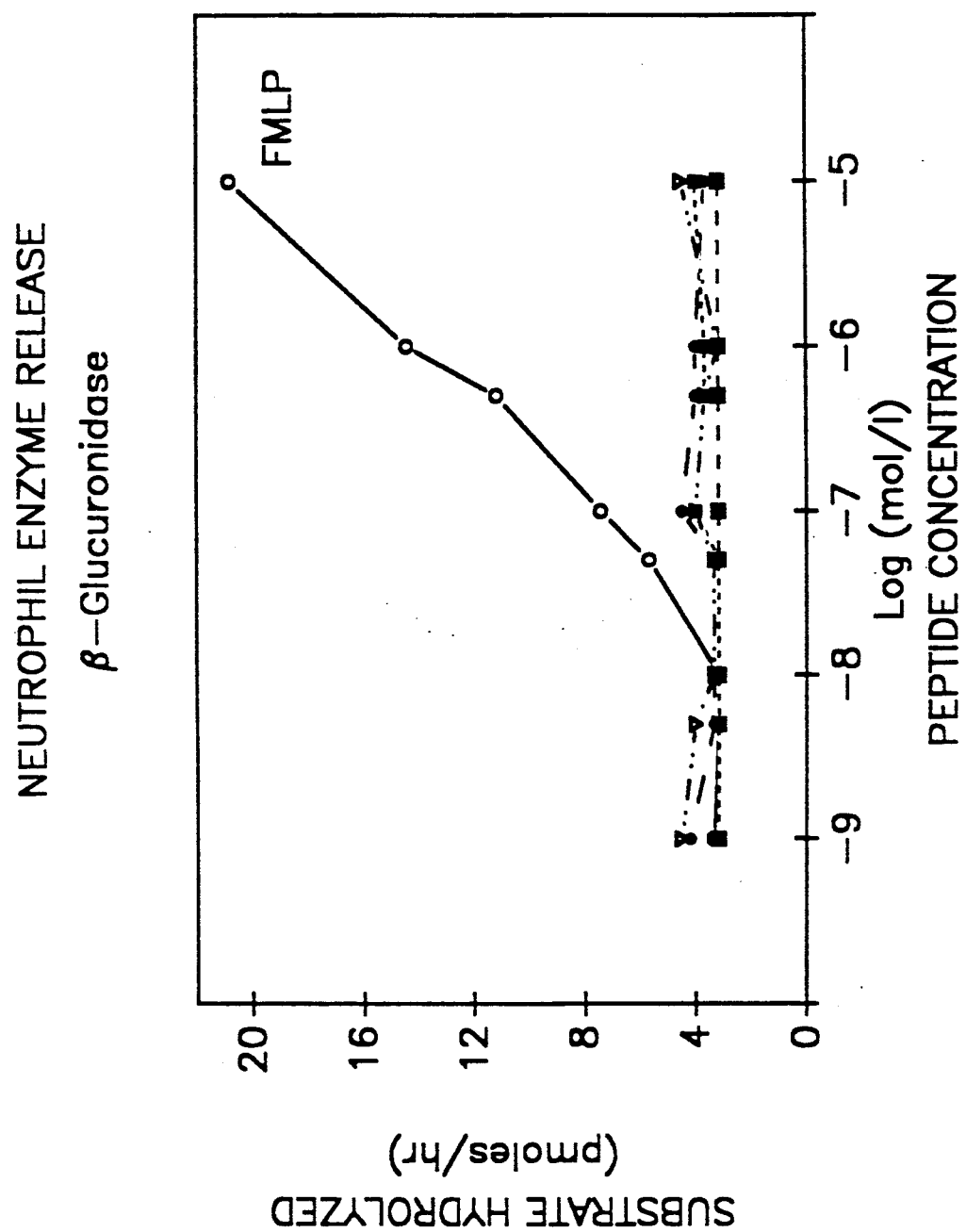
FIG. 3 shows the release of neutrophil $\beta$-D-glucuronidase. None of the synthetic peptides, nor native NAF, caused release of $\beta$-D-glucuronidase from the cells. FMLP used as a control shows that stimulated release from the cells was possible. All assays were performed in duplicate and the graph represents typical data from three experiments.

The ability of native NAF and the synthetic peptides to induce the release of β-D-glucuronidase from cytochalasin B primed neutrophils was examined using a microtiter plate technique. After incubating the primed cells with the peptides the supernatant was examined for β-D-glucuronidase in a dose dependent manner. Neither NAF nor any of the synthetic peptides caused the cells to degranulate (FIG. 3).

Enzyme Assay

β-D-glucuronidase was measured by determining the change in absorbance of phenolphthalein β-D-glucuronide (Sigma Chemical Co.) at 540 nm by the method of Gianetto and DeDuve.[24] The results were expressed as picomoles of substrate hydrolysed per hour.

Bronchoalveolar Lavage Fluids and Lung Edema Fluids

Patients with the Adult Respiratory Distress Syndrome (ARDS) were identified by high permeability pulmonary edema characterized by rapidly developing diffuse lung infiltrates and an inability to oxygenate the arterial blood as a result of a massive insult such as sepsis or trauma in the absence of left-sided heart failure. Bronchoalveolar lavage fluids from these patients were provided by Drs. T. Maunder and R. Martin from The University of Washington in Seattle. Fluids which were directly aspirated from the lungs of patients with high permeability pulmonary edema and cardiogenic pulmonary edema were provided by Dr. M. Mathay, University of California, San Francisco.

NAF was measured in lung wash fluids from patients with ARDS. Early in the disease, when the neutrophils were high, the NAF concentration was also high (Table 3). The mean concentration of NAF in normal subjects was $2.26 \times 10^{-8}$M (S.E.=0.35). In patients with early ARDS, bronchoalveolar lavage fluid NAF concentration was $16.68 \times 10^{-8}$M (S.E.=0.64). The concentration of NAF was statistically significantly higher in bronchoalveolar lavage fluids obtained early in the patients course than late (Table 3). The patients with early ARDS included both survivors and non-survivors, while the patients with late ARDS included only survivors. The cell population in the patients with early ARDS was predominantly neutrophils, but the cell population in bronchoalveolar lavage fluids from patients with late ARDS (survivors) had returned to a macrophage population.

Figure 4:
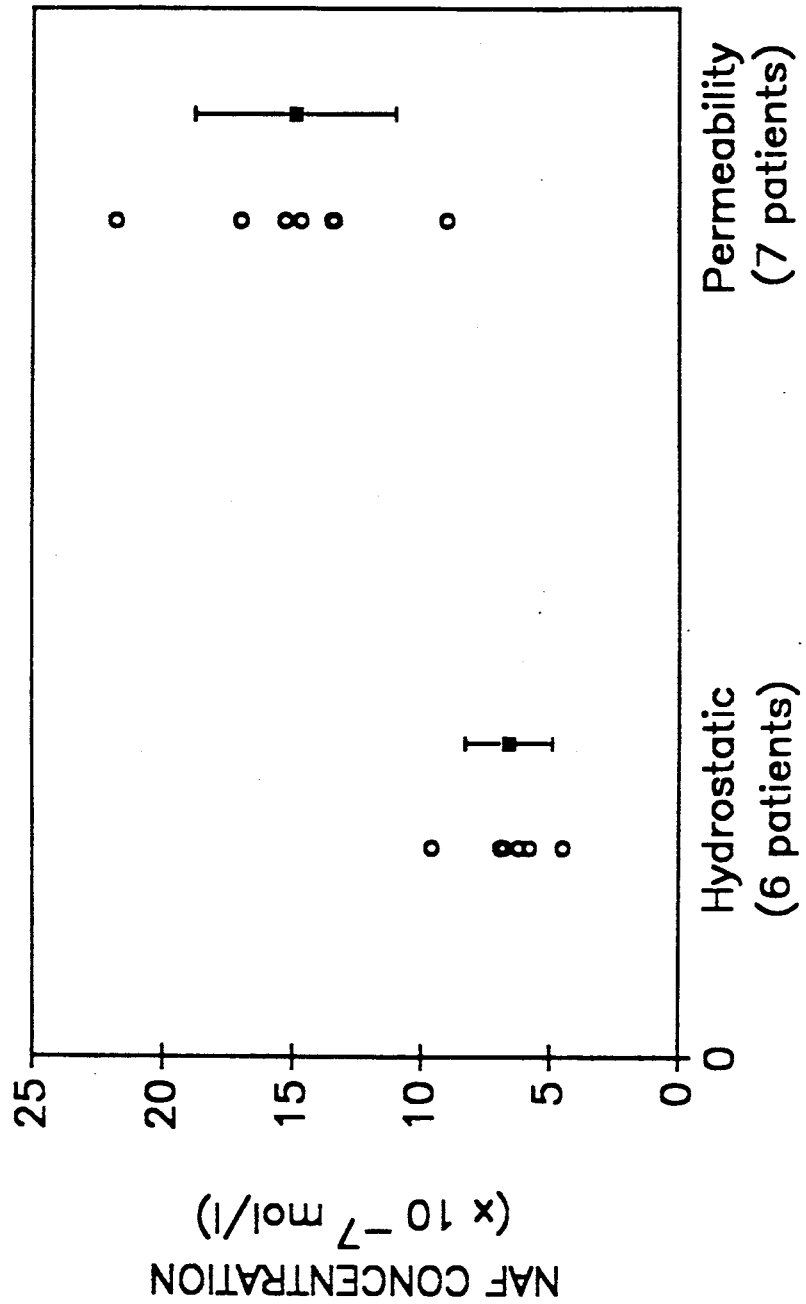
FIG. 4 shows NAF concentration in fluids aspirated from the airways of patients with hydrostatic pulmonary edema or high permeability pulmonary edema (ARDS).

In a separate study, NAF was measured in fluids aspirated without the addition of washing fluid directly from the lungs of patients with ARDS or with hydrostatic pulmonary edema. The patients distributed into a bimodal distribution. The patients with high permeability pulmonary edema had higher concentrations than the patients with hydrostatic pulmonary edema (FIG. 4). Neutrophils in the fluids corresponded to the NAF concentration.

In these studies, overlapping peptides were synthesized which spanned nearly the entire sequence of NAF. None of these peptides had the ability to attract neutrophils or to release azurophilic granule enzymes from them.

The synthetic peptides did not induce chemotaxis, but two of them inhibited chemotaxis. These data suggested the possibility that NAF requires two binding sites to induce full chemotaxis. Tanaka et al.[25] who synthesized three inactive peptides corresponding to residues (7-37), (30-72) and (17-37) of the NAF sequence did not find that any of their synthetic peptides inhibited chemotaxis. However, in the present invention, two of the peptides, NAF (3-25) and NAF (44-72), were able to reduce neutrophil chemotaxis due to the whole recombinant NAF molecule.

TABLE 3

NAF CONCENTRATION IN LUNG WASHES
(Molar Concentration × $10^8$)

| | NORMAL<br>n = 12 | ARDS EARLY<br>n = 10 | ARDS LATE<br>n = 10 |
|---|---|---|---|
| Mean | 2.26 | 16.86* | 2.43** |
| Std. Error | 0.35 | 7.25 | 0.64 |

*A t test of the differences between means showed that NAF concentration was significantly greater in EARLY ARDS than in NORMAL lung lavages (p = 0.019)
**A t test of the differences between means showed that NAF concentration in LATE ARDS was not significantly different from NORMAL (p = 0.404), but was significantly lower than in EARLY ARDS lung lavage fluids (p = 0.0314)

These observations are not readily explained, however, the larger peptides may fold into tertiary structures which are unlike the native molecule. Furthermore, recently published data[26] suggest that the amino-terminal end of NAF is important for its function.

In addition, native NAF failed to release β-D-glucuronidase from cytochalasin B-treated neutrophils. This observation is similar to the findings of Willems and colleagues[14] but different from those of Schröder and colleagues.[7] There are many examples in the literature of functions which were imputed to cytokines which were purified from cells, but which could not be demonstrated using recombinant cytokines. The most likely explanation is that "purified" NAF contained contaminants. However, it is possible that recombinant NAF may be processed differently from native NAF by the cells which synthesize it.

Measurement of NAF in bronchoalveolar lavage fluids from normal subjects and subjects with ARDS showed that NAF was higher in Bronchoalveolar lavage fluids from patients with early ARDS who had large numbers of neutrophils but not from patients with late ARDS who had a dominantly macrophage cell population. In addition, when fluid was aspirated from the airways without adding washing fluid, patients with high permeability pulmonary edema had larger amounts of NAF than patients with hydrostatic pulmonary edema. Therefore, NAF coincides with the high neutrophil counts in high permeability pulmonary edema. The dominant theory about one of the causes of lung injury in patients with ARDS is that the enzymes and oxidants released from neutrophils injure the lungs.[27-29] Most animal models of ARDS require neutrophils to cause the lung injury.[30, 31] Therefore, it is very possible that patients with ARDS would benefit from treatment with the peptides described herein which inhibit the chemotactic effects of NAF. If other forms of inflammation are also caused by NAF, they also may be benefited by therapy with these peptides.

The citations appearing in the application and to which full references are given below are hereby incorporated by reference into this application.

REFERENCES

[1] M. Thelen, P. Peveri, P. Kernen, V. von Tscharner, A. Walz, M. Baggiolini, FASEB J. 2, 2702 (1988).

[2] T. Yoshimura, K. Matsushima, S. Tanaka, et al., PNAS 84, 9233 (1987).

[3] A. Walz, P. Peveri, H. Aschauer, M. Baggiolini, Biochem. Biophys. Res. Commun. 149, 755 (1987).

[4] J. Van Damme, J. Van Veeumen, G. Opdenakker, A. Billiau, J. Exp. Med. 167, 1364 (1988).

[5] Wall Street Journal, Nov. 20, 1989.

[6] J. J. Oppenheim, K. Matsushima, T. Yoshimura, E. J. Leonard, R. Neta, Agents Actions 26, 134 (1989).

[7] J.-M. Schröder, U. Mroweitz, E. Morita, E. Christophers, J. Immunol. 139, 3474 (1987).

[8] C. G. Larsen, A. O. Anderson, E. Appella, J. J. Oppenheim, K. Matsushima, Science 243, 1464 (1989).

[9] J. Schmid, C. Weissmann, J. Immunol. 139, 250 (1987).

[10] N. Mukaida, M. Shiroo, K. Matsushima, J. Immunol. 143, 1366 (1989).

[11] J. Kowalski, D. T. Denhardt, Mol. Cell. Biol. 9, 1946 (1989).

[12] K. Matsushima, K. Morishita, T. Yoshimura, et al, J. Exp. Med. 167, 1883 (1988).

[13] P. Peveri, A. Walz, B. DeWald, M. Baggiolini, J. Exp. Med. 167, 1547 (1988).

[14] J. Willems, M. Joniau, S. Cinque, J. Van Damme, Immunology 67, 540 (1989).

[15] I. Lindlay, H. Aschaver, J.M. Seifert, C. Lam, W. Brunowsky, E. Kownatzki, M. Thelen, P. Peveri, B. DeWald, V. von Tscharner, A. Walz, M. Baggioliri, Proc. Natl. Acad. Sci. USA 85, 9199 (1988).

[16] Sticherling, M., J.-M. Schröder, E. Christophers, J. Immunology 143, 1628 (1989).

[17] A. Boyum, Scand. J. Clin. Lab. Invest. 21, (1968).

[18] A. B. Cohen, D. E. Chenoweth, T. E. Hugli, Am. Rev. Respir. Dis. 126, 241 (1982).

[19] C. K MacArthur, E. J. Miller, A. B. Cohen, J. Immunol. 139, 3456 (1987).

[20] A. B. Cohen, C. MacArthur, S. Idell, et al, Am. Rev. Resp. Dis. 137, 1151 (1988).

[21] S. Zigmond, J. Hirsch, J. Exp. Med. 137, 387 (1973).

[22] R. Snyderman, M. C. Pyke, in: In vitro methods in cell mediated and tumor immunity, B. R. Bloom, J. R. David, Eds. (Academic Press, New York, 1976), pp. 651-661.

[23] I. Goldstein, S. Hoffstein, J. Gallin, G. Weissmann, Proc. Nat. Acad. Sci. USA 70, 2916 (1973). R. Gianetto, C. DeDuve, Biochem. J. 59, 433 (1955).

[25] S. Tanaka, E. A. Robinson, T. Yoshimura, K. Matsushima, E. J. Leonard, E. Appella, FEBS Lett. 236, 467 (1988).

[26] K. Suzuki, A. Koshio, M. Ishida—Okawaja et al., Biochem. Biophys. Res. Commun. 163, 1298 (1989).

[27] W. McGuire, R. G. Spragg, A. B. Cohen, C. G. Cochrane, J. Clin. Invest. 69, 543 (1982).

[28] S. Idell, A. B. Cohen, Clinics in Chest Med. 6, 459 (1985).

[29] S. Idell, U. Kucich, A. Fein, et al, Amer. Rev. Resp. Dis. 132, 1098 (1985).

[30] L. J. Carpenter, K. J. Johnson, R. G. Kunkel, R. A. Roth, Tox. and Appl. Pharmacol. 91, 22 (1987).

[31] R. B. Fox, J. R. Hoidal, D. M. Brown, J. E. Repine, Am. Rev. Resp. Dis. 123, 521 (1982).

What is claimed is:

1. A peptide consisting essentially of 15 to 35 amino acids having a sequence contained in neutrophil activating factor, said peptide being an antagonist of neutrophil activating factor and further being without chemotactic activity.

2. The peptide of claim 1, wherein the amino acid sequence is 22 to 28 amino acids.

3. The peptide of claim 1 defined further as comprising an amino acid sequence corresponding to amino acid sequence 3-25 of human neutrophil activating factor.

4. The peptide of claim 1 defined further as comprising the amino acid sequence:

KELRCQCIKTYSKPFHPKFIKEL or functionality equivalent amino acids.

5. The peptide of claim 1 defined further as comprising an amino acid sequence corresponding to amino sequence 44-72 of human neutrophil activating factor.

6. The peptide of claim 1 defined further as comprising the amino acid sequence:

SDGRELCLDPKENWVQRVVEKFLKRAENS or functionality equivalent amino acids.

7. A peptide consisting essentially of the amino acid sequence:

KELRCQCIKTYSKPFHPKFIKEL

8. A peptide consisting essentially of the amino acid sequence:

SDGRELCLDPKENWVQRVVEKFLKRAENS

9. A method of preventing neutrophil chemotaxis, comprising exposing neutrophils in a biological fluid to an amount of at least one peptide of claim 1, said amount being sufficient to prevent neutrophil chemotaxis.

10. The method of claim 9, wherein the peptide comprises an amino acid sequence corresponding to amino acid sequence 3-25 of active human neutrophil activating factor.

11. The method of claim 9, wherein the peptide comprises an amino acid sequence corresponding to amino acid sequence 44-72 of native human neutrophil activating factor.

12. The method of claim 9, wherein two peptides are used, a first peptide comprising an amino acid sequence corresponding to segment 3-25 of native neutrophil activating factor and a second peptide comprising an amino acid sequence corresponding to segment 44-72 of native neutrophil activating factor.

13. The method of claim 9, wherein two peptides are used, a first peptide comprises a sequence of:

KELRCQCIKTYSKPFHPKFIKEL or functionally equivalent amino acids,
and a second peptide comprises a sequence of:

SDGRELCLDPKENWVQRVVEKFLKRAENS or functionally equivalent amino acids.

14. A method of preventing neutrophil chemotaxis in an aqueous environment, said method comprising inclusion in said aqueous environment of a biologically effective amount of at least one peptide of claim 1 wherein the biologically effective amount is sufficient to inhibit neutrophil chemotactic activity of human neutrophil activating factor.

15. The method of claim 14, wherein the peptide has an amino acid sequence corresponding to segment 3-25 of human neutrophil activating factor.

16. The method of claim 14, wherein the peptide comprises the amino acid sequence:

KELRCQCIKTYSKPFHPKFIKEL or functionally equivalent amino acids.

17. The method of claim 14, wherein a first and a second peptide are included, the first peptide comprising an amino acid sequence substantially identical with that of segment 3-25 of native human neutrophil activating factor, and the second peptide comprising an amino acid sequence substantially identical with segment 44-72 of native human neutrophil activating factor.

18. The method of claim 17, wherein the first peptide comprises the amino acid sequence:

KELRCQCIKTYSKPFHPKFIKEL or functionally equivalent amino acids, and
the second peptide has an amino acid sequence comprising:

SDGRELCLDPKENWVQRVVEKFLKRAENS or functionally equivalent amino acids.

19. A method of treating bronchial inflammation comprising administering a composition including the peptide of claim 1.

20. The method of claim 19 wherein the bronchial inflammation is adult respiratory distress syndrome.

* * * * *